(12) United States Patent
Weiss et al.

(10) Patent No.: US 8,285,365 B2
(45) Date of Patent: Oct. 9, 2012

(54) INTERVENTIONAL DEVICE FOR RF ABLATION FOR USE IN RF FIELDS

(75) Inventors: Steffen Weiss, Hamburg (DE);
Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 767 days.

(21) Appl. No.: 12/438,144

(22) PCT Filed: Aug. 20, 2007

(86) PCT No.: PCT/IB2007/053311
§ 371 (c)(1),
(2), (4) Date: Feb. 20, 2009

(87) PCT Pub. No.: WO2008/023321
PCT Pub. Date: Feb. 28, 2008

(65) Prior Publication Data
US 2010/0004528 A1 Jan. 7, 2010

(30) Foreign Application Priority Data
Aug. 22, 2006 (EP) .................................. 06119286

(51) Int. Cl.
*A61B 5/05* (2006.01)
(52) U.S. Cl. ........ 600/427; 600/407; 600/410; 600/421; 600/424
(58) Field of Classification Search .................. 600/407, 600/410, 421–427
See application file for complete search history.

(56) References Cited

U.S. PATENT DOCUMENTS

| 6,128,522 A * | 10/2000 | Acker et al. ................. 600/411 |
| 6,246,896 B1 * | 6/2001 | Dumoulin et al. ........... 600/411 |
| 2002/0109503 A1 | 8/2002 | Kestler et al. |
| 2005/0218897 A1 | 10/2005 | Schulz et al. |

FOREIGN PATENT DOCUMENTS

| WO | 02083016 A1 | 10/2002 |
| WO | 2005103748 A1 | 11/2005 |
| WO | 2006003566 A1 | 1/2006 |
| WO | 2006067703 A2 | 6/2006 |

OTHER PUBLICATIONS

Weiss, S., et al.; Transmission Line for Improved RF Safety of Interventional Devices; 2005; MRM; 54:182-189.

* cited by examiner

*Primary Examiner* — Brian Casler
*Assistant Examiner* — Joel Lamprecht

(57) ABSTRACT

A interventional device for RF ablation for use in a RF electrical and/or magnetic field especially of a MR imaging system is disclosed, comprising an ablation catheter which is preferably trackable or can be guided or visualized in the image generated by the MR imaging system by means of a MR micro-coil (102), and which is provided with an ablation electrode (101). The interventional device further comprises a transmission path (103) with line segments (104', 104") and transformers (105) therebetween, for connecting the MR micro-coil (102) in a differential mode with a MR receiver (108) and for connecting a RF amplifier (107) in a common mode with the ablation electrode (101) for conveying RF ablation power.

15 Claims, 2 Drawing Sheets

INTERVENTIONAL DEVICE FOR RF ABLATION FOR USE IN RF FIELDS

FIELD OF THE INVENTION

The invention relates to an interventional device comprising an ablation catheter for RF ablation of body tissue, or a transdermal ablation probe (or needle), e.g. for tumor ablation in the liver, prostate or kidney, or generally for use in electrophysiologic (EP) interventions, and a connected transmission path, wherein the device is provided for use in a RF electrical and/or magnetic field especially of a MR imaging system and especially for visualizing the catheter or probe in a MR image. The invention further relates to a MR imaging system comprising such an interventional device.

BACKGROUND OF THE INVENTION

U.S. Pat. No. 6,246,896 discloses a MRI guided ablation system comprising a tracking coil which serves dual purposes. At first it provides NMR tracking data for the MRI system which is used to help a physician to guide the ablation device into a proper treatment position within the patient, and thereafter it is used by the ablation system to deliver the heat generating energy to the target tissue. In order to achieve this, a switch operated by the MRI system either couples the tracking coil to a receiver in the MRI system when it performs a position measurement by a NMR pulse sequence, or couples it to an ablation control for performing ablation of tissue. As an alternative, the ablation control could be inductively coupled to the tracking coil.

SUMMARY OF THE INVENTION

It has revealed that a disadvantage of the ablation system as discloses in the U.S. Pat. No. 6,246,896 is that catheter tracking and tissue ablation cannot be conducted at the same time. Furthermore, there is a considerable risk that due to RF transmission ($B_1$ field) by the MR system during position measurement (as well as during the normal MR imaging), the ablation device and especially the cable or transmission path connecting the ablation device with the switch or another component of the MRI system is heated up unintentionally (and the adjacent body tissue of the patient as well) due to standing waves on the cable or transmission path, so that the patient can be hurt.

However, there is a great desire for tracking, guiding and visualization of a RF ablation catheter or probe in a MR imaging system. Due to the fact that MR imaging allows for visualization of tissue with good contrast, the tissue ablated during the ablation procedure can be monitored. Furthermore, the cardiac motion and flow dynamics within the tissue to be imaged can be monitored during the ablation procedure as well. This enables acute assessment of cardiac function as the intervention is performed. Moreover, it is possible to record the intracardial electrograms (IEGM) during MR imaging, and with a combined electrophysiology/MR imaging catheter, IEGM recording and active tracking can be performed simultaneously in a purely diagnostic EP procedure.

An object underlying the invention is to provide an interventional device as mentioned in the opening paragraph, in which an undesired heating of the interventional device, especially of the connected cable or transmission path, due to RF standing waves is at least substantially avoided, when guided through a RF electrical and/or magnetic field especially of a MR imaging system, and over which transmission path ablation power can be transmitted to the connected RF ablation catheter or probe.

The object is solved by an interventional device for RF ablation for use in a RF electrical and/or magnetic field, comprising:
- an ablation catheter or probe with an ablation electrode for delivering RF ablation power, and
- a transmission path connected with the ablation catheter or probe, comprising at least two line segments which are electrically coupled by means of at least one coupling element comprising a high pass filter characteristic so that:
- common mode currents induced in the transmission path by the RF field of a first frequency to which the transmission path is exposed, are at least substantially blocked and
- the RF ablation power having a predetermined second RF frequency ($f_A$) which is higher than the first frequency, is at least substantially, or to an extent which is necessary for a desired ablating of a tissue, transmitted over the transmission path.

The interventional device can be realized on the basis of a given coupling element with a given high pass filter characteristic, in which case the second frequency is selected such that a desired amount of ablation power is transmitted over the transmission path as mentioned above, and/or the interventional device can be realized on the basis of a given or desired second frequency, in which case the coupling element and especially its high pass filter characteristic is selected in order to transmit a desired amount of ablation power over the transmission path as mentioned above.

This solution has the advantage that the RF transmission (generation of $B_1$ field for MR imaging) and the feeding of RF ablation power over the transmission path can be conducted at the same time without the occurrence of an undesired heating of the path. Due to the fact that RF transmission can be conducted simultaneously with RF ablation, the tracking or visualization of the ablation catheter or probe (e.g. by means of a known active or passive method) in the MR image is enabled to be conducted simultaneously with the ablation (and/or sclerosis) of tissue, and the tissue which is actually ablated during the ablation procedure can be monitored substantially in realtime or online by intravascular MR imaging.

Another advantage of this solution is that no extra cable is necessary for supplying the RF ablation power to the ablation electrode. By this, a lower profile of the catheter is achieved, and no safety problems due standing waves on a (non existing) RF ablation cable arise.

The subclaims disclose advantageous embodiments of the invention.

The coupling elements according to the embodiments of claims 2 and 3 have the advantage that they can be realized in a comparatively simple manner for the relevant frequencies, so that an appropriate coupling and stray capacity is achieved.

The embodiment according to claim 4 has the advantage that the ablation catheter or probe can be tracked, guided and/or visualized (especially by means of MR signals which are detected by the MR/RF micro-coil) well defined and distinctively in the MR image generated by a MR imaging system.

The embodiments according to claims 5 and 6 have the advantage that only one transmission path or line or cable is necessary for feeding ablation power to the ablation catheter or probe, and for feeding the MR/RF signals which are detected and/or transmitted by the MR/RF micro coil between this coil and the MR/RF receiver and/or transmitter.

The embodiments according to claims 7 and 8 have the advantage that a compact interventional device for MR guided ablation is provided which can be used as a separate unit in different MR imaging systems and independently from a specific kind of such a system.

Finally, according to claim 9, the interventional device according to the invention can be used advantageously in a method for RF ablation and/or sclerosis of body tissue.

Further details, features and advantages of the invention will become apparent from the following description of preferred and exemplary embodiments of the invention which are given with reference to the drawings.

DETAILED DESCRIPTION OF PREFERRED EMBODIMENTS

Figure 1:
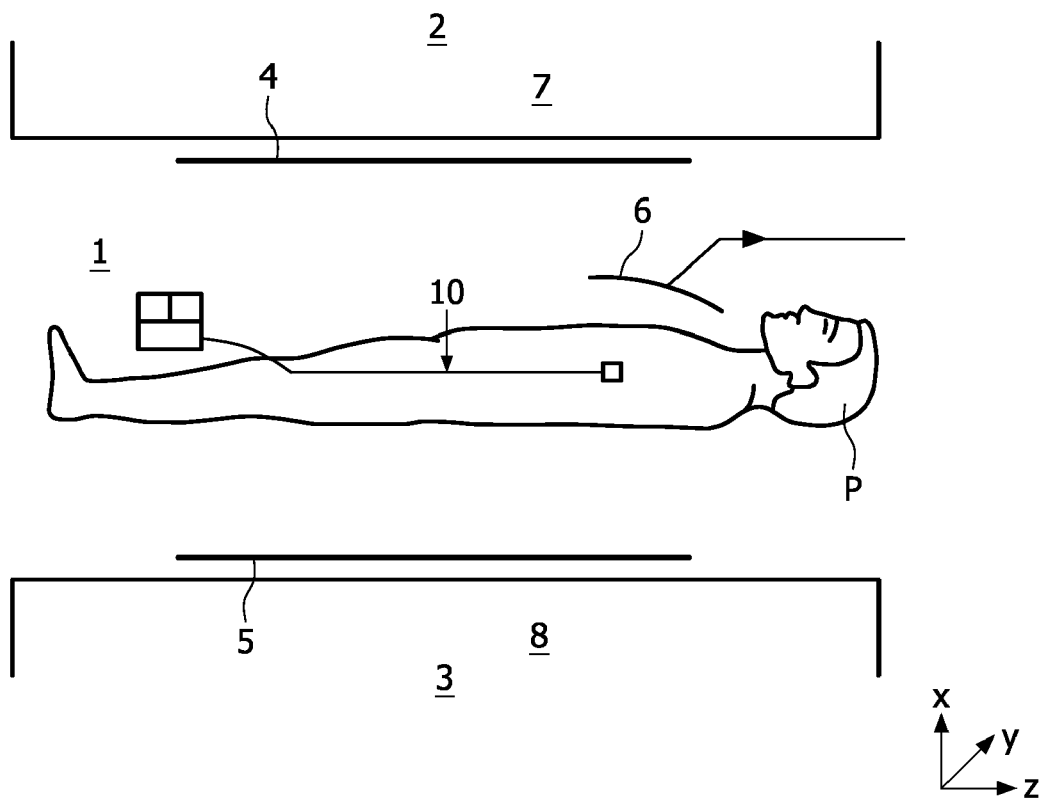
FIG. 1 shows a diagrammatic side elevation of an MR imaging apparatus.

FIG. 1 shows substantial components of a MR imaging system, which are of essential importance for the generation of magnetic fields and RF pulses and for receiving MR relaxation signals in an examination zone 1. Above and underneath the examination zone 1 there are provided respective magnet systems 2, 3 which serve to generate an essentially uniform main magnetic field ($B_0$ field for aligning the nuclear spins in the object to be examined) whose magnetic flux density (magnetic induction) may be in the order of magnitude of from some tenths of Tesla to some Tesla. The main magnetic field essentially extends through a patient P in a direction perpendicular to the longitudinal axis of the patient (that is, in the x direction).

Planar or at least approximately planar RF conductor structures (surface resonators) in the form of RF transmission coils 4 serve to generate RF pulses ($B_1$ field) of the MR frequency whereby the nuclear spins are excited in the tissue to be examined, said RF transmission coils 4 being arranged on the respective magnet systems 2 and 3. MR/RF receiving coils 5 serve to pick up subsequent relaxation events in the tissue; these coils may also be formed by surface resonators provided on one of the magnet systems 2, 3. A common MR/RF surface resonator can also be used for transmission and reception if it is suitably switched over, or the two RF surface resonators 4, 5 can serve for the alternating transmission of RF pulses and reception of MR signals in common.

Furthermore, for the spatial discrimination and resolution of the relaxation (MR) signals emanating from the tissue of a patient P (localization of the excited states) and of the MR signals detected by a MR/RF micro-coil, there is also provided a plurality of gradient magnetic field coils 7, 8 whereby three gradient magnetic fields are generated which extend in the direction of the x axis. A first gradient magnetic field then varies essentially linearly in the direction of the x axis, while a second gradient magnetic field varies essentially linearly in the direction of the y axis, and a third gradient magnetic field varies essentially linearly in the direction of the z axis.

Electrical accessory devices or auxiliary equipments are required for given examinations. Such devices are, for example, MR/RF surface coils 6 which are used in addition or as an alternative to the planar MR/RF receiving coils 5 (body coils) and which are arranged as MR receiving coils directly on the patient P or the zone to be examined. These MR/RF surface coils 6 are generally constructed as flexible pads or sleeves.

Furthermore, in order to carry out the treatment of the patient P or to extract or ablate a tissue sample or to determine tissue parameters, or tumor ablation, use is made of interventional devices comprising an ablation catheter 10 for RF ablation (and/or sclerosis) of body tissue, or a transdermal ablation probe, e.g. for tumor ablation in the liver, prostate or kidney, or generally for use in electrophysiologic (EP) interventions, which is introduced into the patient and whose position is preferably tracked or guided or visualized on a display screen of the MR imaging system.

More in detail, performing RF ablation procedures under MR imaging usually involves two distinct processes: interactive guidance of the RF electrode (e.g. into the targeted tumor) and monitoring the effect of therapy. The justification for using MR imaging for electrode guidance is quite similar to its use to guide biopsy and aspiration procedures, where MR imaging offers advantages related to superior soft tissue contrast, multiplanar capabilities, and high vascular conspicuity that facilitate safe and accurate guidance in selected lesions. The major contribution of MR imaging to RF ablation procedures is its ability to monitor tissue changes associated with the heating process instantaneously, an attribute that is not paralleled by any other currently available imaging modality. Such ability facilitates a controlled approach to ablation by helping to detect inadequately treated tumor foci for subsequent interactive repositioning of the RF electrode during therapy. As such, MR imaging guidance and monitoring enable treatment of the entire tumor on a single-visit basis while avoiding undue overtreatment and preserving often critically needed organ function.

Generally, during a MR-guided EP procedure, four different tasks have to be performed:

1. Real-time MR imaging and catheter tracking must be performed to guide the catheter. This requires frequent transmission of RF pulses by the RF transmission coils 4 of the MR imaging system at the Larmor frequency of 64 MHz for a 1.5 T MR scanner.

2. The position of the catheter must be tracked and visualized on the real-time MR images. This can be performed using an active or passive tracking scheme involving the MR signal of a MR/RF micro-coil at the tip of the catheter in the μV range at 64 MHz.

3. The IEGM signals are measured using bipolar electrodes. These signals are in the 0 to 10 mV range and in the 0 to 500 Hz frequency band (not required for tumor ablation).

4. RF ablation is performed using a unipolar tip electrode (ablation electrode) at the catheter and area surface electrodes on the trunk or at the extremities of the patient. Ablation is usually performed with a distal power of about 30 to about 50 W for about 30 to about 60 s and a frequency of typically about 500 kHz.

As mentioned in the introductory part above, one problem is to transmit the signals described in tasks 2 to 4 above over one cable within the interventional device and without causing standing waves and undesired RF heating of the cable or transmission path due to the transmission of RF pulses for the real-time imaging mentioned under task 1 above.

Figure 2:
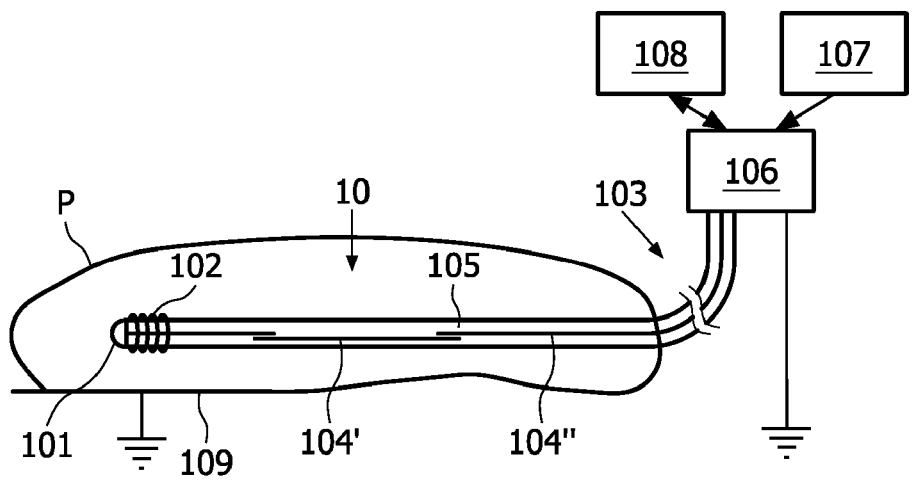
FIG. 2 shows a diagrammatic representation of an interventional device in the form of a catheter system in accordance with the invention.

FIG. 2 shows a diagrammatic representation of an interventional device according to a preferred embodiment of the invention.

It comprises an ablation electrode 101 and a MR/RF micro-coil 102 at the tip of an ablation catheter 10 which is introduced into a patient P, wherein the patient P is positioned on a surface electrode 109. The ablation catheter 10 is connected via a cable or a transmission line or transmission path 103 with a connection unit 106.

In order to avoid an RF heating of the transmission path 103 due to RF pulses ($B_1$ field) transmitted by the RF transmission coils 4 at the Larmor frequency (first frequency), the transmission path 103 comprises a plurality of line segments or sections 104', 104", . . . which are connected with each other by means of each a coupling element 105 which comprises a high pass filter characteristic, preferably in the form of at least one capacitor. The coupling elements 105 are provided for blocking common mode RF currents which are induced by said RF pulses and which may lead to a dangerous RF heating due to standing waves, so that the transmission path 103 is made "MR safe" at the frequency of the RF pulses.

The coupling elements are preferably transformers 105 comprising a capacitor in the form of a stray capacity $C_S$ of the transformer.

Such a transformer-based safe transmission line (STL) can be provided as known in the prior art. For example, an MR safe transmission path comprising line segments which are coupled to each other by a transformer as disclosed in WO2005/103748 can be used. Alternatively, PCB transmission lines and transformers as diclosed in WO2006/003566 and/or transformers in the form of distributed circuit elements which electrically extend over at least a part of adjacent lead or line segments as diclosed in WO2006/067703 can be used as well.

MR signals (especially tracking or local imaging signals) which are received (or detected) by the MR/RF micro-coil 102 and/or RF signals which are transmitted by the MR/RF micro-coil 102 (for the purpose of passive or active localization of the catheter or probe 10 in the MR image) have to be fed via the transmission path 103 and the connection unit 106 to a MR/RF receiver/transmitter 108 (task 2 above). For this purpose, the coupling elements 105 (especially transformers) are provided such that these MR/RF signals can pass the coupling elements 105 in the form of differential mode currents.

Furthermore, a RF amplifier 107 is provided for generating RF ablation power which is fed via the connection unit 106 and the same MR safe transmission path 103 to the ablation electrode 101 (task 4 above).

In order to enable this, the RF amplifier 107 is provided for generating a RF ablation power at a second frequency $f_A$ above the Larmor frequency, for example at a frequency $f_A$=200 MHz or above, so that the common mode of the MR safe transmission path 103 can be used to convey this RF ablation power at least to a desired extent to the ablation electrode 101. Accordingly, the second frequency $f_A$ is selected also in dependence on the transmission characteristic of the at least one coupling element 105. Consequently, the RF ablation is performed at a frequency $f_A$ which is higher than the commonly used ablation frequency band between 300 kHz and 1 MHz as mentioned above under task 4.

In other words, the RF amplifier 107 is connected with the ablation electrode 101 via the connection unit 106 and the transmission path 103 in common mode in order to convey the RF ablation power generated by the RF amplifier 107 at a second frequency $f_A$ well above the Larmor frequency, whereas simultaneously the MR/RF micro-coil 102 is connected with the MR/RF receiver/transmitter 108 via the same transmission path 103 and the connection unit 106 in differential mode in order to convey image information in the form of a tracking or imaging MR signals received or RF signals to be transmitted by the MR/RF micro-coil 102.

Accordingly, the connection unit 106 performs three tasks:
the one way common mode connection for the RF ablation power to the ablation electrode 101,
the differential mode connection for the MR/RF signals to/from the MR receiver/transmitter 108 and
the isolation of the MR/RF receiver/transmitter 108 from the RF ablation power generated by the RF amplifier 107.

The connection unit 106 can be realized in the form of a network of isolators and filters wherein its detailed layout is obvious for a person skilled in the art.

Figure 3:
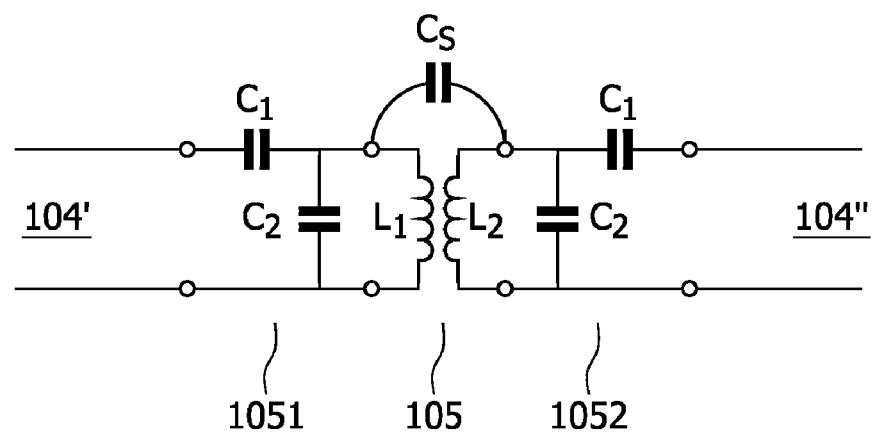
FIG. 3 shows a schematic diagram of a transformer for connecting two cable sections in accordance with the invention and FIG. 4 shows a top and cut view of an exemplary embodiment of such a transformer.

FIG. 3 shows two lead or line segments or sections 104', 104" of the transmission path 103 which are connected to one another by means of a preferred coupling element in the form of a transformer 105. The transformer 105 comprises a first and a second inductance $L_1$, $L_2$ and a stray capacity $C_S$ between both. The frequency $f_A$ of the RF ablation power is selected such that it can pass the transformer 105 in common mode via the stray capacity $C_S$ Consequently, the stray capacity $C_S$ is effective for the common mode transmission of the RF ablation power from the RF amplifier 107 to the ablation electrode 101.

The impedances of the lead segments 104', 104" and of the transformer 105 are matched to each other by means of each one matching network 1051, 1052 which comprises at least one T-, L- and/or π-quadrupole, with at least two impedance elements in the form of a capacitor $C_1$, $C_2$ and/or an inductivity.

Figure 4A:
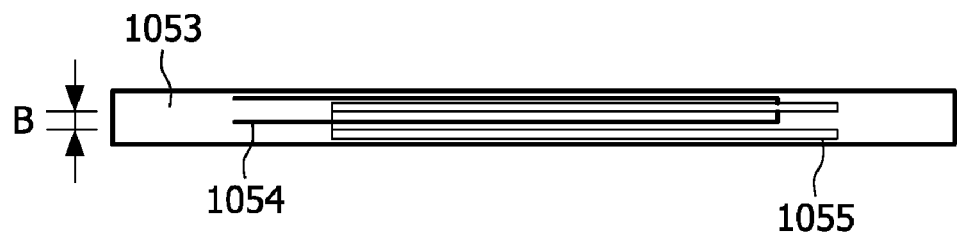
Figure 4B:
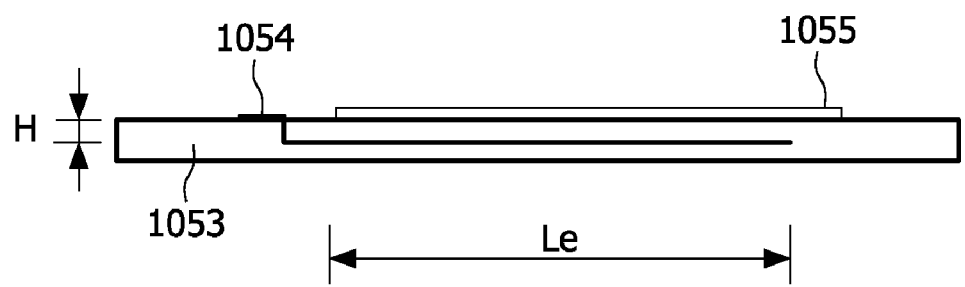

In the following a preferred embodiment of a matching network 1051, 1052, each comprising a first serial capacitor $C_1$ and a second parallel capacitor $C_2$, and a transformer 105 which is shown in FIG. 4(A) in top view and in FIG. 4(B) in side view shall be explained in more details.

The transformer 105 is realized in PCB technology on a substrate 1053 in the form of a first loop 1054 (Cu) and a second loop 1055 (Cu) which overlap each other for inductive coupling, each with a length Le of about 50 mm, a distance B of the lines of a loop of about 0.5 mm, a distance H of the loops of about 0.127 mm and a cross section of the loops of 35×25 μm.

For such an elongated single loop transformer using PCB technology, L=64 nH, k=0.39 and a stray capacity $C_S$=4 pF were measured. The stray capacity $C_S$ of 4 pF represents an impedance of about 200 Ohm at a frequency of about 200 MHz.

Preferably, up to three transformers 105 are distributed along an MR safe transmission line 103 in a catheter of a length of about 1.20 m. The three transformers 105 sum up to a reactance of $X_{Cs}$=600 Ohm. Typical resistance and capacitance of the system comprising the tip electrode, a patient and a ground electrode are $R_P$=100 Ohm and $C_P$=20 nF. The reactance of $C_P$ at 200 MHz is only 0.04 Ohm so that the ohmic losses are dominant. The ohmic losses are mainly localized in a small volume of tissue adjacent to and at the tip electrode. Usually, an RF ablation power of up to 100 W dissipated at $R_P$ is used. This requires a voltage at $R_P$ of 100 V and a current of 1 A, all at 200 MHz. All these values indicate that an effective RF ablation at the catheter tip is possible with this set-up.

At last, the RF conditions at the transformers 105 should be considered. At each transformer 105 ($C_S$=4 pF, $X_{Cs}$=200 Ohm) there is a voltage of about 200 V which is far below the destruction limit of the 127 μm thick Teflon layer between the loops 1054, 1055 of the transformer 105. Also the capacitive tuning and matching network 1051, 1052 ($C_1$, $C_2$ >40 pF) will only see voltages far below their maximum ratings. The common mode series resistance of a transformer 105 is about $R_T$=2 Ohm at 64 MHz, and estimated according to $R_T \sim \sqrt{f}$ with $R_T$=3.5 Ohm at 200 MHz. This results in a thermal dissipation of 3.5 W during the ablation pulse which does not harm the transformer 105.

While the invention has been illustrated and described in detail in the drawings and foregoing description, such illustration and description are to be considered illustrative or exemplary and not restrictive, and the invention is not limited to the disclosed embodiments.

The invention claimed is:

1. An interventional device for RF ablation for use in a RF electrical and/or magnetic field, comprising:
   an ablation catheter or probe with an ablation electrode for delivering RF ablation power, and an MR/RF micro-coil for receiving MR signals and/or for transmitting RF signals, and
   a transmission path connected with the ablation catheter or probe, wherein the transmission path comprises at least two line segments which are electrically coupled by at least one coupling element comprising a high pass filter characteristic so that:
   common mode currents induced in the transmission path by the RF electrical and/or magnetic field of a first frequency to which the transmission path is exposed, are at least substantially blocked,
   the RF ablation power having a predetermined second RF frequency, which is higher than the first frequency, is at least substantially, or to an extent which is necessary for a desired ablating of tissue, transmitted in the form of common mode currents over the transmission path, and
   MR signals and/or RF signals which are received and/or transmitted by the MR/RF micro-coil are conveyed over the transmission path in the form of differential mode currents.

2. The interventional device according to claim 1, wherein the coupling element is a transformer and the high pass filter characteristic is realized by a stray capacity of the transformer, the stray capacity representing a first impedance which is matched to a second impedance of the at least two line segments by at least one matching network located on the transmission path.

3. The interventional device according to claim 2, wherein the transformer is realized in PCB technology on a substrate in the form of a first conductive loop and a second conductive loop which overlap each other for inductive coupling.

4. An interventional device for RF ablation for use in a RF electrical and/or magnetic fields, the device comprising:
   an ablation catheter or probe;
   an ablation electrode mounted to the catheter or probe to deliver ablation power to tissue to be ablated;
   an MR/RF micro-coil for receiving MR signals and/or for transmitting RF signals, for active and/or passive tracking, guiding and/or visualization of the catheter or probe in an MR image generated by an MR imaging system;
   a transmission path extending along the ablation catheter or probe, the transmission path including at least two line segments which are electricaly coupled by a high pass filter which blocks common mode currents induced in the transmission path by the RF electrical and/or magnetic field at a first frequency;
   a source of RF ablation power having a predetermined second RF frequency which is higher than the first frequency, the source of RF ablation power being connected with the transmission path to transmit the RF ablation power as common mode currents of the second frequency over the transmission path to the ablation electrode;
   wherein the MR signals and/or RF signals which are received and/or transmitted by the MR/RF micro-coil are conveyed over the transmission path in the form of differential mode currents, simultaneous with delivering RF ablation power by means of the ablation electrode.

5. The interventional device according to claim 1, further comprising:
   a MR/RF receiver and/or transmitter which is connected with the transmission path for receiving MR signals detected by the MR/RF micro coil and/or for generating RF signals to be transmitted by the MR/RF micro coil.

6. The interventional device according to claim 1, further comprising:
   an RF amplifier for generating the RF ablation power at the second RF frequency, of 200 MHz or more, which RF amplifier is connected with the transmission path.

7. The interventional device according to claim 5, comprising:
   a connection unit for connecting the MR/RF receiver and/or transmitter and the RF amplifier with the transmission path and for decoupling the MR/RF receiver and/or transmitter from the RF ablation power generated by the RF amplifier, the connection unit providing one way common mode connection for the RF ablation power to the ablation electrode and differential mode connection for the MR/RF signals to or from the MR receiver and/or transmitter.

8. The interventional device according to claim 1 for use in a method for RF ablation and/or sclerosis of body tissue and/or tumor ablation.

9. An MR imaging system comprising an interventional device according to claim 1.

10. The interventional device according to claim 2, wherein the at least one matching network comprises at least one T-, L- and/or π-quadrupole, with at least two impedance elements in the form of a capacitor C1, C2, and/or an inductivity.

11. The interventional device according to claim 2, wherein the stray capacity represents an impedance of 200 Ohm at a frequency of 200 Mhz.

12. The interventional device according to claim 4, wherein the transmission path connected with the ablation catheter or probe is blocked from RF heating due to standing waves, the transmission path being MR safe at the frequency of RF pulses.

13. The interventional device according to claim 12, wherein at least one and no more than three transformers are distributed along the MR safe transmission line, wherein the ablation probe or catheter is no more than 1.20 m in length.

14. An interventional device for RF ablating tissue in an examination region of a magnetic resonance imaging system, the interventional device comprising:
   a catheter configured to extend internally through a patient in the examination region to tissue to be RF ablated;
   at least two line segments extending along the catheter;
   at least one filter connected with the line segments to block common mode RF currents induced in the line segments at a Larmor frequency of the magnetic resonance imaging system during imaging;

an RF ablation power supply connected with the line segments to provide common mode RF ablation current at an RF frequency different from the Larmor frequency such that the at least one filter does not block the common mode RF ablation current;

an RF ablation electrode mounted adjacent a tip of the catheter to be positioned by the catheter adjacent the tissue to be ablated based on images generated by the magnetic resonance imaging system, the RF ablation electrode being connected with the line segments to receive the common mode RF ablation current therefrom; and an MR/RF micro-coil mounted adjacent the tip of the catheter and connected with the line segments to at least one of transmit and receive differential mode currents over the line segments.

15. The interventional device according to claim 14, wherein the RF ablation current and the differential mode currents are transmitted on the line segments concurrently.

\* \* \* \* \*